(12) United States Patent
Lee et al.

(10) Patent No.: US 8,250,908 B2
(45) Date of Patent: Aug. 28, 2012

(54) WAVE SENSOR APPARATUS INCLUDING GAS REMOVING UNIT AND METHOD OF DETECTING TARGET MATERIAL IN LIQUID SAMPLE

(75) Inventors: Hunjoo Lee, Seoul (KR); Jaechan Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 582 days.

(21) Appl. No.: 12/485,992

(22) Filed: Jun. 17, 2009

(65) Prior Publication Data
US 2010/0037677 A1 Feb. 18, 2010

(30) Foreign Application Priority Data
Aug. 14, 2008 (KR) ................ 10-2008-0079921

(51) Int. Cl.
*G01N 29/00* (2006.01)
(52) U.S. Cl. ...................................... 73/64.53
(58) Field of Classification Search ............... 73/64.53
See application file for complete search history.

(56) References Cited

U.S. PATENT DOCUMENTS

| | | | |
|---|---|---|---|
| 5,959,191 A | 9/1999 | Lewis et al. | |
| 5,992,215 A | 11/1999 | Caron et al. | |
| 6,260,408 B1 | 7/2001 | Vig et al. | |
| 6,418,783 B2 | 7/2002 | Sunshine et al. | |
| 6,435,007 B1 | 8/2002 | Smith et al. | |
| 2006/0029929 A1 | 2/2006 | Hunt | |
| 2007/0159027 A1 | 7/2007 | Tsai et al. | |
| 2007/0245810 A1 | 10/2007 | Carter et al. | |

FOREIGN PATENT DOCUMENTS

| | | |
|---|---|---|
| JP | 2001-153782 A | 6/2001 |
| KR | 10-2008-0016595 A | 2/2008 |
| KR | 10-2008-0027239 A | 3/2008 |
| WO | 2008/063643 A2 | 5/2008 |

OTHER PUBLICATIONS

Cole M, et al. "Voltage Modulated SAW Microtrap System: Smart Assaying of Biomaterials", 2005 IEEE Sensors, IEEE—Piscataway, NJ, USA, Oct. 31, 2005, pp. 1300-1303, XP010899901, DOI: DOI: 10.1109/ICSENS.2005.1597945, ISBN: 978-0/7803-9056-0.

Chen K, et al., "Determination of urea in urine using a conductivity cell with surface acoustic wave resonator-based measurement circuit", Talanta, Elsevier, Amsterdam, NL, vol. 41, No. 12, pp. 2195-2200, XP026552367, ISSN: 0039-9140, DOI: DOI: 10.1016/0039-9140(94)00197-9 [retrieved on Dec. 1, 1994].

European Patent Office, Partial European Search Report issued on Apr. 8, 2011 in counterpart European Application No. 09167754.2.

European Patent Office, Search Report issued on Jul. 12, 2011 in European Patent Application No. 09167754.2.

*Primary Examiner* — Hezron E Williams
*Assistant Examiner* — Rodney T Frank
(74) *Attorney, Agent, or Firm* — Sughrue Mion, PLLC

(57) ABSTRACT

Disclosed is a wave sensor apparatus including a unit for removing a gas and a method of detecting a target material in a liquid sample, the method including removing a gas in the liquid sample.

22 Claims, 6 Drawing Sheets

US 8,250,908 B2

WAVE SENSOR APPARATUS INCLUDING GAS REMOVING UNIT AND METHOD OF DETECTING TARGET MATERIAL IN LIQUID SAMPLE

CROSS-REFERENCE TO RELATED APPLICATIONS

This application claims the benefit of Korean Patent Application No. 10-2008-0079921, filed on Aug. 14, 2008, in the Korean Intellectual Property Office, the disclosure of which is incorporated herein in its entirety by reference.

BACKGROUND

1. Field

One or more embodiments relate to a wave sensor apparatus including a gas removing unit and a method of detecting a target material in a liquid sample.

2. Description of the Related Art

Sensors that sense a wave signal are known. Examples of these sensors include sensors that measure acoustic waves including surface acoustic waves. For example, a method of sensing a mass deposited on a surface of a piezoelectric resonator is known. A well-known quartz crystal microbalance (QCM) includes the piezoelectric resonator that can detect micro mass. With respect to a small amount of mass, a change in a resonant frequency of the piezoelectric resonator is proportional to a mass change. QCM sensors have been used in detecting humidity in the atmosphere or the presence of other absorption gases, or monitoring the thickness of a thin film. In addition, sensors that use, as a chemically sensitive film on the sensor, molecules of biological origin immobilized on a surface thereof, for example, antibodies, cells, enzymes, nucleic acids, and proteins, are known.

In addition, a sensor that senses a wave signal can be used in measuring a material in a liquid sample. For example, the presence of materials of biological origin, such as proteins or cells, is required to be detected in a liquid phase. The measurement of the material in the liquid phase may be affected by properties of the liquid sample in addition to the material, for example, the weight, viscosity and density of the liquid. In addition, the measurement thereof may be affected by other materials besides a target material existing in the liquid sample, for example, the presence of drops of a gas such as air. The gas drops or gas bubbles existing in the liquid sample may significantly affect a wave applied to the liquid sample.

Thus, in a wave sensor apparatus, such as a LOVE-mode acoustic wave sensor, which detects a fine change in mass through a change in a wave signal, there is a need to develop an apparatus and method for accurately and efficiently detecting a target material by monitoring impacts of properties of the liquid itself in the liquid sample and other materials besides the target material.

SUMMARY

One or more embodiments include a wave sensor apparatus for efficiently measuring a target material in a liquid sample.

One or more embodiments include a method of efficiently detecting a target material in a liquid sample.

Additional aspects will be set forth in part in the description which follows and, in part, will be apparent from the description, or may be learned by practice of the invention.

To achieve the above and/or other aspects, one or more embodiments may include a method of detecting a target material in a liquid sample by using a wave, the method including: supplying an input wave signal to a first liquid sample that does not comprise the target material, and measuring a first output wave signal from the first liquid sample; supplying an input wave signal to a second liquid sample that is subject to the detecting the target material, and measuring a second output wave signal from the second liquid sample; and comparing the first output wave signal with the second output signal to determine whether there is a difference between the signals, wherein the input wave signals supplied to the first and the second liquid samples are identical; wherein the first output wave signal is used as a signal base line; and wherein the existence of the difference indicates a presence of the target material in the second liquid sample.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
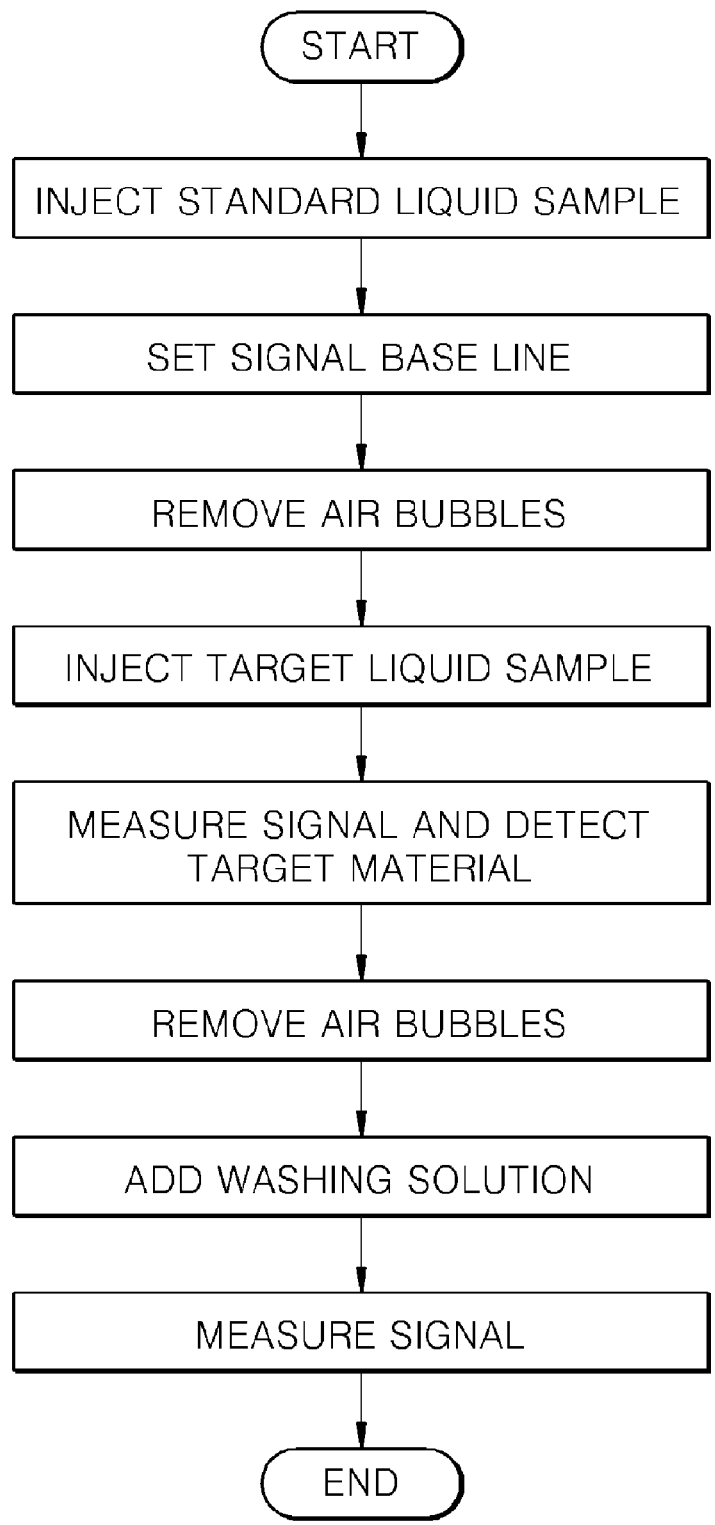
FIG. 1 is a flowchart for explaining a method of detecting a target material in a liquid sample, according to an embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

One or more embodiments provide a method of detecting a target material in a sample including supplying a wave signal to a standard liquid sample that does not include a target material, and measuring the wave signal from the standard liquid sample.

The wave may be an acoustic wave. An acoustic wave is a wave in which energy is transmitted by a change in a phase of a medium in an elastic medium. For example, the acoustic wave may be a surface acoustic wave. A surface acoustic wave refers to a wave propagating along a surface of an elastic substrate. For example, an electrical wave forms a mechanical wave on the surface of an elastic substrate, the mechanical wave is changed by physical, chemical or electrical reactions between the surface of the elastic substrate and the target material, and the change is measured, thereby allowing for detection and/or analysis of the target material. That is, the surface acoustic wave can be measured by a change in the surface acoustic wave, generated when the standard liquid sample and target liquid sample and materials included therein are bound to the surface of the elastic substrate, or generated due to a change in physical or chemical properties thereof.

The surface acoustic wave is supplied to (input wave signal) and measured from (output wave signal) a material with a surface (hereinafter, sometimes referred to as "surface material") included in the standard liquid sample (first liquid sample) and in the target liquid sample (second liquid sample). The material that binds the target material (hereinafter, sometimes referred to as "target binding material") may or may not be immobilized on the surface of the surface material. The target binding material may include any materials that can bind the target material specifically or non-specifically. The surface of the surface material may be a surface on which the target binding material is immobilized, a surface on which the target binding material is not immobilized, or a surface on which a material that does not bind the target material included in the target liquid sample is immobilized. That is, for example, a target binding material may be immobilized on the surface of the surface material. The target binding material may be an antibody or antigen, a nucleic acid, an enzyme or enzyme substrate, a receptor or ligand, or the like, which binds the target material. In addition, the target binding material is not separately immobilized on the surface of the material. A specific bond, non-specific bond or non-covalent bond interaction such as van der Waals interaction between the surface and the target material may cause a change in the wave applied to the standard and target liquid samples.

The surface material may comprise a substance that causes a change in a wave due to the interaction between the target material and the surface of the material, for example, a change in a wave signal generated by causing a mass change. For example, the material may be a piezoelectric substrate.

The wave signal can be measured using characteristics of the wave, such as frequency, phase, and/or amplitude. The wave signal may be provided by a wave providing unit, such as a wave function generator. The wave providing unit may include a unit that generates a wave signal, for example, an oscillator, such as a sine wave oscillator that generates a sine wave signal, a pulse oscillator that generates a pulse signal, or a resonator. The wave providing unit may produce a wave signal by oscillating the elastic substrate. For example, the wave providing unit may be connected to a wave measurement container, and may be electrically connected to a piezoelectric substrate installed in the wave measurement container. The wave providing unit generates piezoelectric distortion by applying an electrical signal, for example, a radio frequency (RF) signal to an inter-digitated transducer (IDT) electrode on the piezoelectric substrate, thereby providing the piezoelectric substrate or a liquid that contacts the piezoelectric substrate with a wave signal, for example, a surface acoustic wave.

When the target material is included in a liquid medium, the target material comprises a substance that allows the presence or amount of the target material in liquid to be detected such that by changing characteristics of a wave that is incident on the liquid medium, the wave emitted from the liquid medium is measured. The target material may be a biomaterial. Examples of the biomaterial include nucleic acids, proteins, sugars, viruses, cells, and cell organelles. The nucleic acids may be DNA, RNA, PNA, or oligonucleotide. The biomaterial may be derived from living organisms, or synthesized or semi-synthesized.

The standard liquid sample does not contain the target material, and the target liquid sample is expected to contain the target material and thus is subject to the detection method.

For example, the standard liquid sample may have the same properties as those of the target liquid sample, for example, pH, viscosity and ionic strength, except that it does not include the target material. However, providing a standard liquid sample that has the same properties as those of the target liquid sample but not including the target material may be impractical or impossible. Thus, the standard liquid sample may be a liquid sample that does not include the target material or contain a predetermined or known amount of the target material and has properties similar to those of the target liquid sample, for example, similar pH, viscosity and ionic strength. The standard liquid sample is used for providing a base line of the measured wave signal, and the properties to be similar between the standard and target liquid samples may easily be selected by one of ordinary skill in the art. The standard liquid sample may be a buffer that can include a known amount of the target material. The known amounts may be a gradient of known amounts. The wave signal value measured from the standard liquid sample can be used as a base line of the wave signal value measured from the target liquid sample that includes the target material.

The measurement of the wave signal is performed such that the wave signals generated from the standard and target liquid samples are measured using a wave signal measurement unit. The wave signal measurement unit measures characteristics of the wave, for example, frequency, phase, and/or amplitude. For example, the wave signal measurement unit may include a unit that can record a change in a frequency shift generated from interaction of biomolecules (target material) and the surface of the surface material and analyze the change, such as, an oscillator circuit, a frequency counting unit, or a wave measuring circuit.

In addition, the method of detecting a target material in a sample includes using the signal value measured from the standard liquid sample as a signal base line, supplying a wave signal to a target liquid sample that includes a target material, and measuring the wave signal from the target liquid sample.

The wave, wave signal, target material, standard liquid sample and the measurement of the wave signal are the same as described above.

The wave signal value measured from the standard liquid sample is used as a base line for the wave signal value measured from the target liquid sample. This is for correcting a change in the wave caused from properties of the liquid, such as the viscosity or density of a medium, except for a change in the wave generated by the target material in the target liquid sample.

In addition, the method of detecting a target material in a sample includes detecting the target material from the obtained wave signal value.

The wave, wave signal and target material are the same as described above.

The detecting the target material may be performed by comparing the wave signal values between the standard sample and the target sample and confirming, for example, a change in the wave signal value specific to the target material. In addition, the detecting the target material may be performed, for example, such that by confirming a change in a characteristic wave signal value according to the concentration of the target material, the concentration of the target material is measured. The change in the wave signal value specific to the target material may be obtained such that by using a series of liquid samples each including a known or predetermined level of the target material, as a control, a wave is supplied to the liquid sample in the same manner as in the embodiment described above, the wave generated therefrom is measured, and then a change in wave characteristics specific to the target material is confirmed.

Before measuring the wave signal of the target liquid sample, gas bubbles may be removed from the liquid sample. For example, the liquid may include a gas due to inflow of air during transfer of the liquid, and such gas is removed to increase accuracy of the wave measurement. The gas may be included in the liquid sample or in a process of handling a wave measuring device used in the measurement of the wave signal.

The wave signal of the target liquid sample may be measured after the standard liquid sample is removed from the wave measurement container, and then the target liquid sample is introduced into the wave measurement container. In this case, before the introduction of the target liquid sample into the wave measurement container, the gas included in the target liquid sample or between the target liquid sample and the standard liquid sample may be removed. For example, the removal of the gas may be performed by transferring some of the target liquid sample to another container from a path through which the target sample liquid is introduced, instead of the wave measurement container. The other container may be a waste chamber, and a channel connected to the waste chamber may exist between the wave measurement container and the path through which the target liquid sample is introduced.

When a signal to be measured is a surface acoustic wave, the measurement of the surface acoustic wave signal may further include subtracting the surface acoustic wave signal value measured from the surface material on which the target binding material is not immobilized or the surface material on which a material (hereinafter, sometimes referred to as "nonreactive material") that does not bind any materials included in the target liquid sample is immobilized (hereinafter, such surface material is sometimes referred to as "standard surface material" or "standard substrate"), from the surface acoustic wave signal value measured from the surface material on which the target binding material is immobilized (hereinafter, such surface material is sometimes referred to as "active surface material" or "active substrate"). Thus, errors or inaccuracies of the measured wave signal for interaction between the target material and the target binding material may be removed or minimized. The derivations or inaccurate results may be caused by interaction between the target material and the surface of the active substrate and the standard substrate, and the weight, viscosity, density or electrical properties of the target liquid sample. The material that does not bind any materials contained in the target liquid sample may be exemplified by bovine serum albumin (BSA). The detection of the target material may be performed according to a change in the wave signal according to time. In addition, the active and standard substrates may be included in a single wave measurement container or separate wave measurement containers.

One or more embodiments may include a method of detecting a target material in a sample by a wave, the method including: providing a target liquid sample which is to be tested for a target material using a wave signal and measuring the wave signal generated from the target liquid sample; and detecting the target material from the obtained wave signal value. The measuring the wave signal may include removing a gas in the target liquid sample.

The wave, wave signal, target material, measurement of the wave signal and detecting of the target material are the same as described above.

The measuring of the wave signal includes removing the gas in the target liquid sample. The gas in the target liquid sample, for example, air is removed to increase the accuracy of the measurement of the wave signal. The gas may be included in the target liquid sample, or introduced into the target liquid sample when the wave sensor apparatus is handled. For example, the gas may be introduced into the target liquid sample during the handling of the wave sensor apparatus by opening or closing of a valve or a movement of a fluid in a channel. The removal of the gas may be performed when or after the standard liquid sample is removed from the wave measurement container, and after the target liquid sample is introduced into the wave measurement container. In this case, before the introduction of the target liquid sample into the wave measurement container, the gas included in the target liquid sample may be removed. For example, the removal of the gas may be performed by transferring some of the target liquid sample to another container from a path through which the target sample liquid is introduced, instead of the wave measurement container. The other container may be a waste chamber used for bypassing the target liquid sample from the path through which the target liquid sample is introduced into the wave measurement container, before the introduction of the target liquid sample into the wave measurement container.

To achieve the above and/or other aspects and advantages, one or more embodiments may include a wave sensor apparatus including: a container into which a liquid sample is introduced; a wave providing unit which supplies the container with a wave signal; and a wave measuring unit that measures the wave signal from the container. The wave sensor apparatus may further comprise a unit used to remove a gas in the liquid sample.

In particular, the wave sensor apparatus includes the container into which the liquid sample is introduced. The container provides a space in which the liquid sample can be introduced. The container may be, but is not limited to, in the form of a chamber or channel. The chamber may be in the form of a chamber or channel included in a microfluidic device. In this case, the introduction of the liquid sample may be performed through a channel and by using a pump, or providing an hydraulic or fluidic pressure, and such movement may be controlled by a valve. Thus, the wave sensor apparatus may include the pump and/or valve that are operably connected to the container. A microfluidic device is well-known in the art. In general, the term "microfluidic device" used herein refers to a structural body including: a chamber that can confine a small amount of a fluid; a channel through which the fluid can flow; a valve that can control a flow of the fluid; and various functional units that can implement a certain function by receiving the fluid. In addition, the wave sensor apparatus may include a liquid sample flow control device including a program including consecutive commands that order initiation and stopping of operation of the pump and/or valve. The microfluidic device includes a substrate in the form of a disk, which can rotate around a rotation axis. The substrate in the form of a disk may include at least one chamber, a channel that connects these chambers, and a control unit disposed between the channels, which can control the movement of the fluid, for example, a valve. Thus, the wave sensor apparatus may be formed in the microfluidic device in the form of a disk.

The container may include a surface material. A target binding material may be immobilized on a surface of the surface material. The surface material may have two or more surfaces, of which one or more, or all have the target binding material immobilized thereon, while remaining surfaces do not have the target binding material immobilized thereon. The surface material may be immobilized on the container, or may float in the liquid sample. For example, the surface material may be in the form of a flat plate, a bead, or sphere. The surface material is directly or indirectly connected to a wave providing unit, for example, an oscillator to be operable.

The liquid sample includes a standard (or reference) liquid sample that does not include a target material or a known amount of the target material, and/or a target liquid sample that is to be tested for the existence or the amount of a target material.

When the target material is included in a liquid medium, the target material includes a substance that allows the presence or amount of the target material in liquid to be detected such that by changing characteristics of a wave that is incident on the liquid medium. The wave emitted from the liquid medium is measured to determine a change in characteristics of the wave. The target material may be a biomaterial. Examples of the biomaterial include nucleic acids, proteins, sugars, viruses, cells, and cell organelles. The nucleic acids may be DNA, RNA, PNA, or oligonucleotide. The cells may be a eukaryotic cell such as plant or animal cell and a prokaryote cell such as bacteria. The biomaterial may be derived from living organisms, or synthesized or semi-synthesized.

The standard liquid sample does not include the target material, and the target liquid sample includes the target material. For example, the standard liquid sample may have the same properties as those of the target liquid sample, for example, pH, viscosity and ionic strength, except that it does not include the target material. In addition, preparing a standard liquid sample that has the same properties as those of the target liquid sample but does not include the target material may be impractical or impossible. Thus, the standard liquid sample may be a liquid sample that does not include the target material and has properties similar to those of the target liquid sample, for example, similar pH, viscosity and ionic strength. The standard liquid sample is used for providing a base line of the measured wave signal, and the similarity between properties of the standard and target liquid samples may easily be selected by one of ordinary skill in the art. The standard liquid sample may be a buffer that can include the target material in a known amount. The wave signal value measured from the standard liquid sample can be used as a base line of the wave signal value measured from the target liquid sample that includes the target material.

The wave sensor apparatus includes the wave providing unit that supplies the container with the wave signal.

The wave providing unit may include a unit that generates a wave signal, for example, an oscillator, such as a sine wave oscillator that generates a sine wave signal, a pulse oscillator that generates a pulse signal, or a resonator. The wave providing unit may produce a wave signal by oscillating an elastic substrate. For example, the wave providing unit may be connected to the container, and may be electrically connected to a piezoelectric substrate installed in the container. The wave providing unit generates piezoelectric distortion by applying an electrical signal, for example, a radio frequency (RF) signal to an inter-digitated transducer (IDT) electrode on the piezoelectric substrate, thereby providing the piezoelectric substrate or a liquid that contacts the piezoelectric substrate with a wave signal, for example, a surface acoustic wave.

The wave may be an acoustic wave. An acoustic wave is a wave in which energy is transmitted by a change in a phase of a medium in an elastic medium. For example, the acoustic wave may be a surface acoustic wave. A surface acoustic wave refers to a wave propagating along a surface of an elastic substrate. For example, an electrical wave forms a wave on the surface of an elastic substrate, such as an electrical wave or mechanical wave, the formed wave is changed by physical, chemical or electrical reactions between the surface of the elastic substrate and the target material, and the change is measured, thereby allowing for detection and/or analysis of the target material. That is, the surface acoustic wave can be measured by a change in the surface acoustic wave, generated when the standard liquid sample and target liquid sample and materials included therein are bound to the surface of the elastic substrate, or generated due to a change in physical or chemical properties thereof.

The surface acoustic wave is measured from a surface material included in the standard liquid sample and in the target liquid sample. The target binding material may be immobilized or may not be immobilized on the surface of the surface material. The target binding material may include any materials that can bind the target material specifically or non-specifically. The surface of the surface material may be a surface on which the target binding material is immobilized, a surface on which the target binding material is not immobilized, or a surface on which a material ("non-reactive material") that does not bind any materials contained in the target liquid sample is immobilized. That is, the target binding material, for example, a binding material may be immobilized on the surface of the material. The binding material may be an antibody or antigen, a nucleic acid, an enzyme or substrate, a receptor or ligand, or the like, which binds the target material. In addition, the material that binds the target material is not separately immobilized on the surface of the material, and a chemical bond or simple interaction (e.g., van der Waals interaction) between the surface and the target material, according to properties of the surface itself, may cause a change in the wave applied into the standard and target liquid samples. In addition, the material that does not bind the material included in the target liquid sample may be immobilized on the surface of the material. The surface material may comprise a substance that causes a change in a wave due to the interaction between the target material and the surface, for example, a change in a wave signal generated by causing a mass change. For example, the material may be a piezoelectric substrate.

The wave sensor apparatus includes the wave measuring unit that measures the wave signal from the container.

The wave measuring unit measures characteristics of the wave, for example, frequency, phase and/or amplitude. For example, the wave signal measurement unit may include a unit that can record a change in a frequency shift generated from interaction of biomolecules with the binding molecule or the surface of the surface material and analyze the change, such as, an oscillator circuit, a frequency counting unit, or a wave measuring circuit. The wave measuring unit is directly connected to the liquid sample, or indirectly connected to the liquid sample through the container to be operable, and thus the wave generated from the liquid sample can be measured.

The wave sensor apparatus may further include a unit used for removing a gas included in the target liquid sample introduced into the container, or between the standard liquid sample and the target liquid sample.

The unit may be a sonicator disposed in the container or a sonicator disposed in a channel or chamber used for loading the liquid sample into the container. The sonicator can remove a gas in the liquid sample introduced into the container, or remove a gas in the liquid sample in the channel or chamber used for introducing the liquid sample into the container, in order to remove the gas before the introduction of the liquid sample into the container.

The unit may also be a waste chamber connected to a path for introducing the liquid sample into the container to be in fluid communication therebetween. For example, the water chamber may be connected to a channel that connects a liquid sample storing chamber and the container to be in fluid communication therebetween. The wave sensor apparatus may be a microfluidic device, and the waste chamber may be connected to a microchannel through which the liquid sample is introduced into the container to be in fluid communication therebetween. Before the liquid sample is loaded into the container, some of the liquid sample is transferred to the waste chamber, whereby a gas existing in a path through which the liquid sample is introduced into the container, for example, a channel, may be removed. The transfer of the target liquid sample into the waste chamber may be controlled using a fluidic control unit, for example, a valve and pump. The fluidic control unit may include a program that directs an order of opening and closing of the valve and operation of the pump.

The gas in the liquid sample, for example, air, is removed by the unit, thereby increasing the accuracy of the measurement of the wave signal.

The wave sensor apparatus may include at least one chamber of a target liquid sample chamber in which the target liquid sample including the target material is stored, a standard liquid sample chamber in which the standard liquid sample is stored, and a washing chamber including a washing solution. The at least one chamber is connected to the container to be in fluid communication therebetween.

The standard liquid sample chamber may be the same as or different from the washing chamber. When the standard liquid sample is the same as the washing solution, the standard liquid sample chamber may be the same as the washing chamber. The standard liquid sample chamber, washing chamber and target liquid sample chamber is connected to the container via a channel. The waste chamber may be connected to the channel to be in fluid communication therebetween at a position closer to the container than the standard liquid sample chamber, washing chamber and target liquid sample chamber.

The standard liquid sample and target liquid sample are the same as described above. The washing solution is used to wash the wave measurement container from which the standard liquid sample or target liquid sample is removed. The washing solution may be a buffer, for example, phosphate buffered saline (PBS).

The wave sensor apparatus may further include the fluidic control unit, for example, the pump and valve. The standard liquid sample chamber, target liquid sample chamber and washing chamber may be connected via the channel. The pump is a unit that can provide a driving force for the fluid flow. For example, the pump may apply positive air pressure or negative air pressure. The valve is installed at the chambers or in the channel connected between the chambers, thereby controlling the fluid flow between the chambers. The pump and valve may be connected to a fluidic control unit or fluidic control system.

FIG. 1 is a flowchart for explaining a method of detecting a target material in a liquid sample, according to an embodiment.

Referring to FIG. 1, a standard liquid sample is added to a wave sensor apparatus according to an embodiment. Then, a base line is set based on characteristics of a wave signal measured from the standard liquid sample, for example, frequency, phase and/or amplitude. In this regard, the standard liquid sample may be a liquid sample, buffer, or washing solution, which has properties similar to those of the standard liquid sample. After the base line is set, a gas between the standard liquid sample and a target liquid sample, or a gas in the target liquid sample is removed before or when the target liquid sample is added to the wave sensor apparatus. A unit for removing the gas may be, but is not limited to, another container, for example, a waste chamber. That is, by controlling a valve or pump, the gas between the target liquid sample and the standard liquid sample is removed such that the gas is moved to the waste chamber in a path through which the target liquid sample is introduced into the wave sensor apparatus. After or at the same time when the gas is removed, the target liquid sample is added to the wave sensor apparatus, and the wave signal measured from the target liquid sample based on the base line is detected. In the method according to the present embodiment, selectively, the wave sensor apparatus is washed using a washing solution after the detection is terminated, and after a gas generated in the wave sensor apparatus is removed, the wave signal can be repeatedly measured and detected. In this case, a gas between the target liquid sample and the washing solution is also moved to the waste chamber to be removed. Thus, inflow of the gas into the wave sensor chamber can be prevented.

Figure 2:
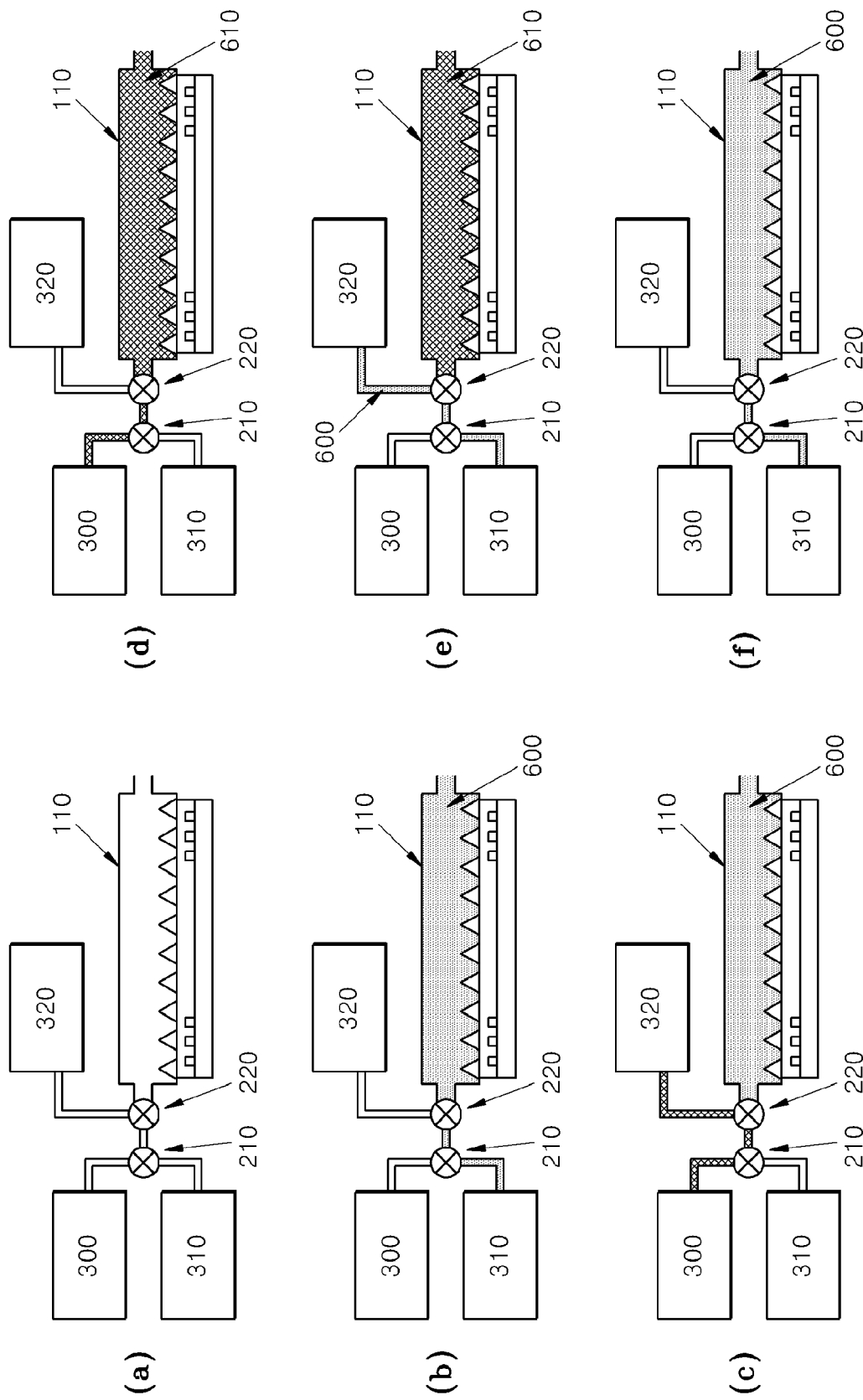
FIGS. 2(a) to 2(f) are a series of diagrams for explaining a method of detecting a target material in a liquid sample by using a wave sensor apparatus, according to an embodiment.

FIGS. 2(a) to 2(f) are a series of diagrams for explaining a method of detecting a target material in a liquid sample by using a wave sensor apparatus, according to an embodiment. In the present embodiment, a standard liquid sample is the same as a washing solution. Referring to FIG. 2(a), the wave sensor apparatus includes a target liquid sample chamber 300 in which the target liquid sample is stored, a standard liquid sample chamber 310 in which a standard liquid sample is stored, a waste chamber 320, and a wave measurement container 110. The target liquid sample chamber 300, the standard liquid sample chamber 310, the waste chamber 320, and the wave measurement container 110 are connected to one another via a channel so as to be in fluid communication therebetween. The channel includes a first channel extending from the target liquid sample chamber 300, a second channel extending from the standard liquid sample chamber 310, and a third channel extending from the waste chamber 320. The first channel and the second channel are merged to form a first fusion channel, and the first fusion channel is merged with the third channel to form a second fusion channel. A first 3-way valve 210 is installed at a position where the first and second channels are merged, thereby controlling an introduction of the target liquid sample or standard liquid sample into the first fusion channel. In addition, a second 3-way valve 220 is installed at a position where the first fusion channel is merged to the third channel, thereby controlling an introduction of the target liquid sample and/or standard liquid sample to the waste chamber 320 or the wave measurement container 110. The wave measurement container 110 includes a surface material, for example, a piezoelectric substrate 100 (Refer to FIG. 3). A target binding material 120 (Refer to FIG. 3) (active substrate) or a material (not shown) that does not bind materials included in the target liquid sample (standard substrate) may be immobilized on the piezoelectric substrate 100 (Refer to FIG. 3). The wave measurement container 110 is connected to a wave providing unit 140, such as a wave function generator (Refer to FIG. 3). The wave providing unit 140 (Refer to FIG. 3) may be an oscillator, a vibrator, or a resonator. In addition, the wave measurement container 110 may include a wave measurement unit (not shown) that is operably connected to the wave measurement container 110. The wave measurement unit may be an amplitude meter, a frequency meter, or a phase meter. The wave measurement container 110 further includes an outlet (now shown) for discharging the liquid samples. The outlet is disposed at a surface of the wave measurement container 110, and may be connected via a channel to another chamber into which the sample discharged from the wave measurement container 110 is introduced. The outlet may simply function as a final outlet of the wave sensor apparatus. The exhaust of the liquid sample through the outlet may be controlled by a valve that is included in or connected to the outlet, and a pump that is included in or connected to the wave sensor apparatus.

Figure 3:
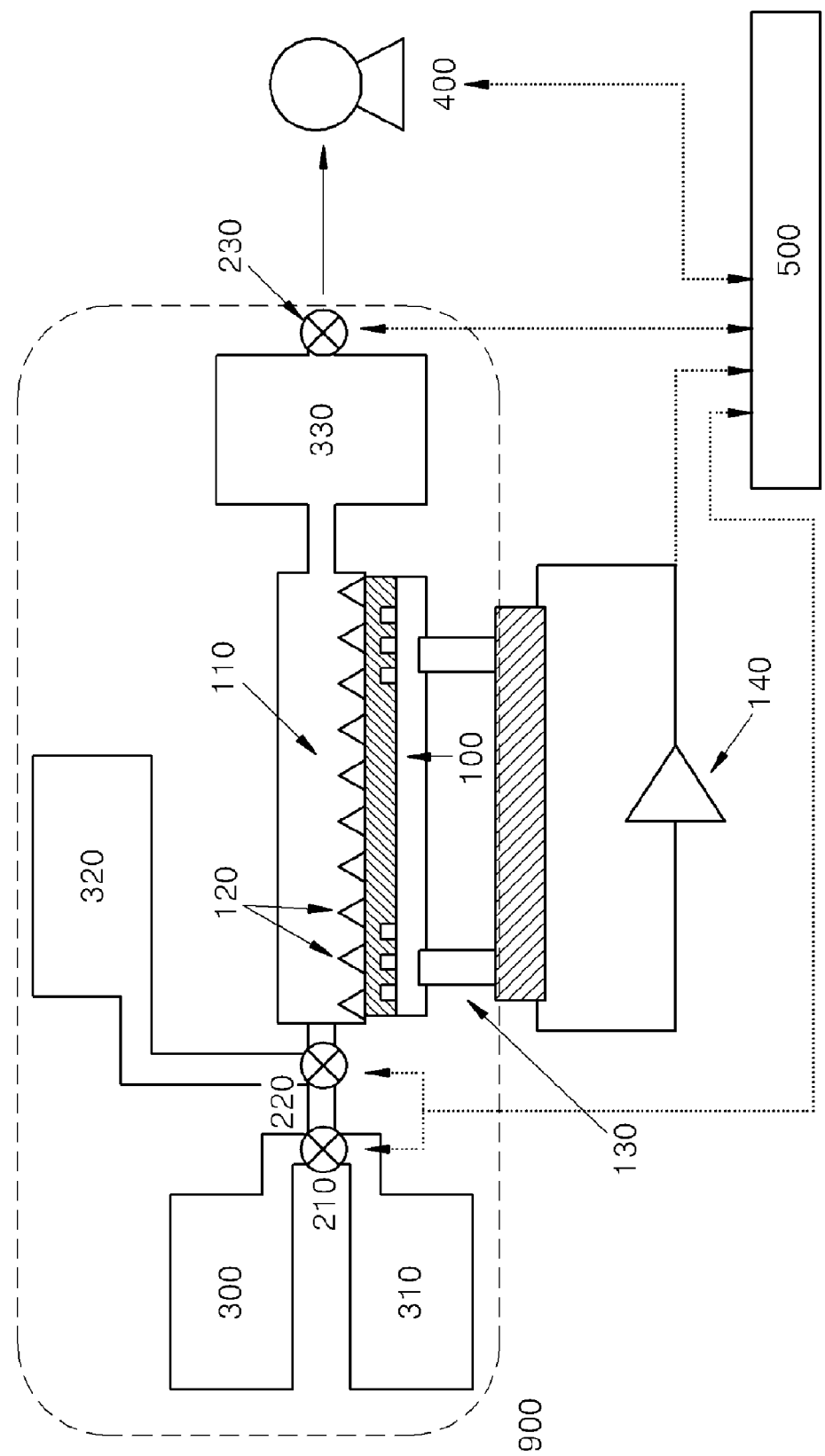
FIG. 3 is a diagram of a wave sensor apparatus according to an embodiment.

In the present embodiment, as illustrated in FIG. 2(b), a standard liquid sample 600 is introduced into the wave measurement container 110 of the wave sensor apparatus, and a surface acoustic wave is supplied to the piezoelectric substrate 100 (Refer to FIG. 3) in the wave measurement container 110 by using the wave providing unit 140 (Refer to FIG. 3). Then, the surface acoustic wave emitted from the piezoelectric substrate 100 (Refer to FIG. 3) in the wave measurement container 110 is measured until the measurement value of the surface acoustic wave becomes stable. The measured surface acoustic wave signal value is used as a base line in subsequent measurement processes. In order to introduce the standard liquid sample 600 into the wave measurement container 110, a port of the first 3-way valve connected to the target liquid sample chamber 300 is closed, a port of the first 3-way valve connected to the standard liquid sample chamber 310 is opened, a port of the second 3-way valve 220 connected to the waste chamber 320 is closed, and a port of the second 3-way valve 220 connected to the wave measurement container 110 is opened, thereby transferring the standard liquid sample 600 to the wave measurement container 110. The transfer of the standard liquid sample 600 may be performed by a pump that applies a negative pressure or a positive pressure.

Next, referring to FIG. 2(c), the standard liquid sample 600 is removed from the wave measurement container 110, the port of the first 3-way valve 210 connected to the target liquid sample chamber 300 is open, and the port of the first 3-way valve 210 connected to the standard liquid sample chamber 310 is closed. Then, the port of the second 3-way valve 220 connected to the waste chamber 320 is open, and the port of the second 3-way valve 220 connected to the wave measurement container 110 is closed. In this state, a target liquid sample is transferred from the target liquid sample chamber 300 to remove a gas included in the first fusion channel. The removal of the standard liquid sample 600 from the wave measurement container 110 may be controlled by closing the port of the second 3-way valve 220 connected to the wave measurement container 110, and opening a valve (not shown) that is included in or connected to the outlet of the wave measurement container 110. The transfer of the standard liquid sample 600 may be performed by a pump that applies a negative pressure or a positive pressure.

Next, referring to FIG. 2(d), the port of the first 3-way valve 210 connected to the target liquid sample chamber 300 is opened, and the port of the first 3-way valve 210 connected to the standard liquid sample chamber 310 is closed. Then, the port of the second 3-way valve 220 connected to the waste chamber 320 is closed, and the port of the second 3-way valve 220 connected to the wave measurement container 110 is opened. In this state, a target liquid sample 610 is transferred to the wave measurement container 110.

Next, a surface acoustic wave is supplied to the piezoelectric substrate 100 (Refer to FIG. 3) in the wave measurement container 110 by the wave providing unit 140 (Refer to FIG. 3), and the surface acoustic wave emitted from the piezoelectric substrate 100 (Refer to FIG. 3) in the wave measurement container 110 is measured using a wave measurement unit (not shown). In this regard, the value measured in operation FIG. 2(b) is used as a base line of the surface acoustic wave. Through this process, the presence or amount of the target material in the target liquid sample may be more accurately measured because the measurement is performed after the gas in the target liquid sample is removed.

The method of detecting a target material in a liquid sample by using a wave sensor apparatus may further include selectively removing the target liquid sample in the wave measurement container 110 and washing the wave measurement container 110. Referring to FIG. 2(e), the port of the first 3-way valve 210 connected to the target liquid sample chamber 300 is closed, the port of the first 3-way valve 210 connected to the standard liquid sample chamber 310 is opened, the port of the second 3-way valve 220 connected to the waste chamber 320 is opened, and the port of the second 3-way valve 220 connected to the wave measurement container 110 is closed. In this state, the standard liquid sample 600 in the standard liquid sample chamber 310 is transferred to remove the gas included in the first fusion channel. Next, the target liquid sample 610 in the wave measurement container 110 is removed. The removal of the standard liquid sample 600 and the target liquid sample 610 from the wave measurement container 110 is the same as described above.

Next, referring to FIG. 2(f), the port of the first 3-way valve 210 connected to the target liquid sample chamber 300 is closed, the port of the first 3-way valve 210 connected to the standard liquid sample chamber 310 is opened, the port of the second 3-way valve 220 connected to the waste chamber 320 is closed, and the port of the second 3-way valve 220 connected to the wave measurement container 110 is opened. In this state, the standard liquid sample 600 in the standard liquid sample chamber 310 is transferred to remove the standard liquid sample 600 in the wave measurement container 110. The removal of the standard liquid sample 600 from the wave measurement container 110 is the same as described above.

FIG. 3 is a detailed diagram of the wave sensor apparatus described with reference to FIGS. 2(a) through 2(e) according to an embodiment.

Referring to FIG. 3, the wave sensor apparatus according to the present embodiment includes the target liquid sample chamber 300 in which the target liquid sample is stored, the standard liquid sample chamber 310 in which the standard liquid sample is stored, the waste chamber 320, and the wave measurement container 110. The target liquid sample chamber 300, the standard liquid sample chamber 310, the waste chamber 320, and the wave measurement container 110 are connected to one another via a channel so as to be in fluid communication therebetween. The channel includes the first channel extending from the target liquid sample chamber 300, the second channel extending from the standard liquid sample chamber 310, and the third channel extending from the waste chamber 320. The first channel and the second channel are merged to form the first fusion channel, and the first fusion channel is merged with the third channel to form the second fusion channel. The first 3-way valve 210 is installed at a position where the first and second channels are merged, thereby controlling an introduction of the target liquid sample or standard liquid sample into the first fusion channel. In addition, the second 3-way valve 220 is installed at a position where the first fusion channel is merged with the third channel, thereby controlling an introduction of the target liquid sample and/or standard liquid sample to the waste chamber 320 or the wave measurement container 110. The active substrate or standard substrate is immobilized on a surface of the wave measurement container 110. The wave measurement container 110 is connected to the wave providing unit, for example, a RF-connector 130 and a wave providing unit 140, such as an oscillator connected to the RF-connector 130, through a bottom material of the wave measurement container 110. In addition, the piezoelectric substrate 100 is installed on a surface of the wave measurement container 110, and a target binding material (for example, antibody) capable of binding a target material (for example, antigen) is immobilized on the piezoelectric substrate 100. In addition, the wave sensor apparatus further includes an outflow chamber 330 connected to the outlet of the wave measurement container 110. The outflow chamber 330 is connected to the wave measurement container 110 to be in fluid communication therebetween, thereby accommodating the same and target liquid samples that are flown out to the outflow chamber 330. The outflow chamber 330 includes a third 3-way valve 230. The wave sensor apparatus may include a unit (not shown) for measuring the wave generated from the piezoelectric substrate 100 of the wave measurement container 110 on which the target binding material 120 that binds a target material (active substrate) or does not bind materials included in the target liquid sample (standard substrate) is immobilized.

The wave sensor apparatus may also include a pump 400 connected to the outflow chamber 330. Although the pump 400 illustrated in FIG. 3 applies a negative pressure, it is possible to use a pump that is installed in front of the target liquid sample chamber 300 and the standard liquid sample chamber 310, thereby applying a positive pressure towards the wave measurement container 110 from the target liquid sample chamber 300 and the standard liquid sample chamber 310.

The wave sensor apparatus may also include a fluid flow control unit 500 that can control a fluid flow in the wave sensor apparatus. The fluid flow control unit 500 may be a unit that controls operation of the first, second and third 3-way valves 210, 220 and 230 and the pump 400. For example, the fluid flow control unit 500 may be a switch device, and may include a unit including a program that directs an order of the opening and closing and initiation or termination of operation of the first, second and third 3-way valves 210, 220 and 230 and the pump 400 and for implementing directions included in the program, such as a switch device.

The wave sensor apparatus may be configured such that a part thereof is formed in the form of a cartridge 900 and is combined with the other elements, thereby being operable when combined together. For example, the cartridge 900 may include the target liquid sample chamber 300, the standard liquid sample chamber 310, the waste chamber 320, the wave measurement container 110 to which a RF-connector is connected, the outflow chamber 330, and a channel formed between these chambers and the container to allow fluid communication therebetween. The cartridge 900 may be connected to an external device that includes the first, second and third 3-way valves 210, 220 and 230, the pump 400, and the fluid flow control unit 500.

Figure 4:
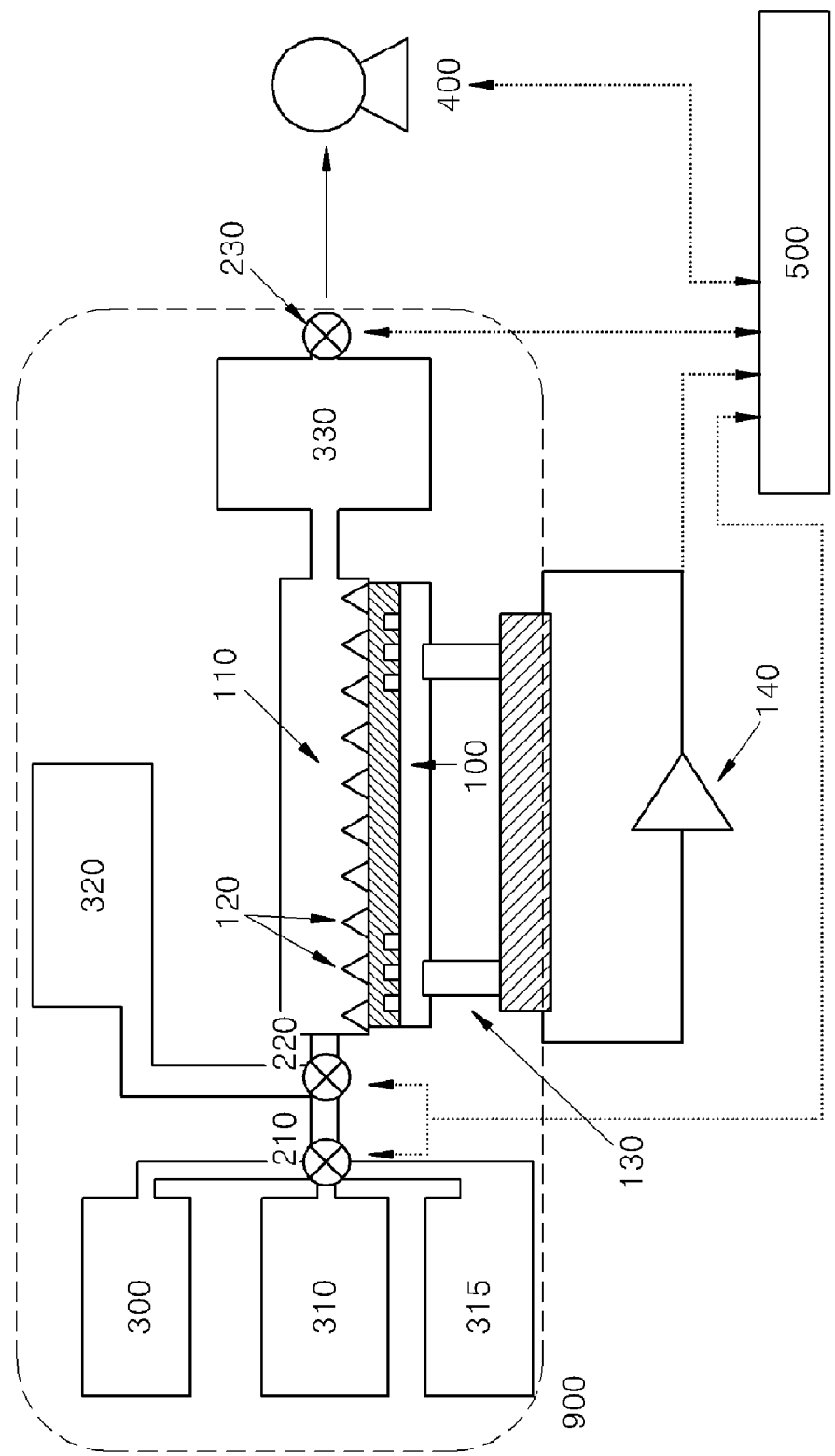
FIG. 4 is a diagram of a wave sensor apparatus according to another embodiment.

FIG. 4 is a diagram of a wave sensor apparatus according to another embodiment.

Referring to FIG. 4, the wave sensor apparatus according to the present embodiment has the same structure as that of the wave sensor apparatus illustrated in FIG. 3, except that it further includes: a washing chamber 315 that is installed in font, in order of operation, of the wave measurement container 110; a third channel extending from the washing chamber 315; and a 4-way valve that is installed at a position where the first, second and third channels are merged into one channel. The washing chamber 315 includes a washing solution stored therein, and the washing solution may be used to wash the inside of the wave sensor apparatus, for example, channels and/or the wave measurement container 110. The washing solution may be, for example, phosphate buffered saline (PBS), but is not limited thereto.

EXAMPLE 1

Difference Between Base Lines in Gas and Liquid Phases

To detect a target material in a liquid sample, a base line is set by using a standard liquid sample because a base line in a liquid phase is different from a base line in a gas phase.

A wave sensor apparatus used herein was the wave sensor apparatus illustrated in FIG. 3 including an active substrate in which a target binding material was immobilized on a surface of the active substrate.

A wave measurement container of the wave sensor apparatus included the active substrate and a standard substrate. The active substrate included a HbsAg antigen immobilized on the surface thereof as the material that binds the target material, and the standard substrate included a material that does not bind materials included in a target liquid sample, such as Bovine serum albumin (BSA) immobilized thereon. Both substrates were included in a single wave measurement container. A RF-connector and an oscillator connected thereto were connected to a bottom surface of the wave measurement container. If a surface acoustic wave is provided using the oscillator, the surface acoustic wave is transmitted to the surface of the active and standard substrates in the wave measurement container through the RF-connector.

Before a standard liquid sample was introduced into the wave measurement container, a surface acoustic wave of 198 MHz was supplied to the wave measurement container through the oscillator, and a change in frequency according to time of the surface acoustic wave generated from the active and standard substrates was measured using an oscillator circuit to measure a fundamental frequency in a gas phase. Then, a PBS solution (8 g NaCl, 0.2 g KCl, 1.44 g $Na_2HPO_4$ and 0.24 g $KH_2PO_4$ in 800 ml $H_2O$, pH 7.4) was introduced into the wave measurement container as the standard liquid sample, and a fundamental frequency in a liquid phase was measured in the same manner as in the measurement of the fundamental frequency in the gas phase. A change in frequency in the wave measurement container was measured using the oscillator circuit for 50 seconds at 25° C. at an atmospheric pressure. Then, while a 100 μl PBS solution (8 g NaCl, 0.2 g KCl, 1.44 g $Na_2HPO_4$ and 0.24 g $KH_2PO_4$ in 800 ml $H_2O$, pH 7.4) was supplied to the wave measurement container, a change in frequency was measured using the oscillator circuit for 150 seconds.

Figure 5:
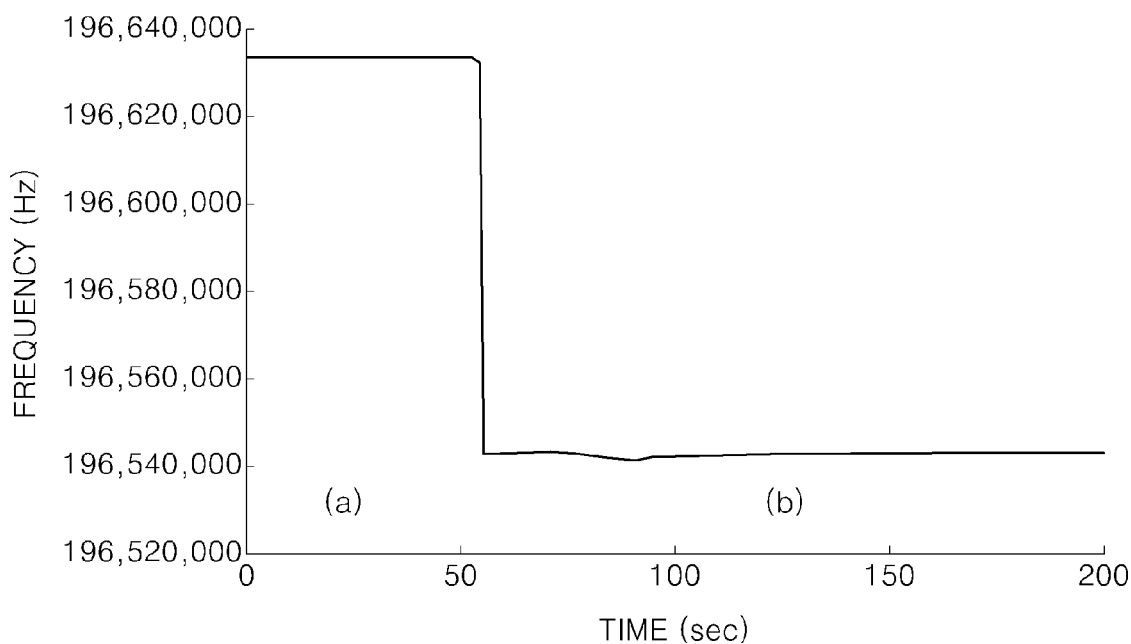
FIG. 5 is a graph showing how a phase change affects a change in frequency of a surface acoustic wave.

FIG. 5 is a graph showing the effects of a phase change on the change in frequency of a surface acoustic wave. In FIG. 5, the area (a) denotes a frequency in the gas phase measured in the active substrate, and area (b) denotes a frequency in the liquid phase measured in the active substrate. Referring to (a) and (b) of FIG. 5, the frequency of the surface acoustic wave in the liquid phase is about 85,000 Hz less than the frequency thereof in the gas phase. From the result, it can be seen that a difference between the frequencies measured in the gas and liquid phases needs to be taken into consideration to detect the target material in the liquid sample.

EXAMPLE 2

Impact of Target Material and Air Bubbles on Surface Acoustic Wave

A base line of a wave measurement container was set using a standard liquid sample, and an introduction of a target liquid sample into the wave measurement container and washing of the container using a washing solution were repeatedly performed to measure a surface acoustic wave.

A wave sensor apparatus which is the same to one used in Example 1 was used. An active substrate including a HbsAg antigen immobilized on a surface thereof as a target binding material, and a standard substrate including a material that does not bind materials included in a target liquid sample, such as BSA, immobilized thereon, were included in a single wave measurement container. First, a PBS solution (8 g NaCl, 0.2 g KCl, 1.44 g $Na_2HPO_4$ and 0.24 g $KH_2PO_4$ in 800 ml $H_2O$, pH 7.4) was supplied to the wave measurement container. Then, a frequency of the surface acoustic wave emitted from the standard substrate in the wave measurement container (thin line, refer to FIGS. 6A and 6C) and a frequency of the surface acoustic wave emitted from the active substrate in the wave measurement container (thick line, refer to FIGS. 6A and 6C) were measured using the oscillator circuit, and the measured value was used as a base line. Sixty (60) seconds after the base line was set, a PBS solution including 100 ng HBsAb/ml (8 g NaCl, 0.2 g KCl, 1.44 g $Na_2HPO_4$ and 0.24 g $KH_2PO_4$ in 800 ml $H_2O$, pH 7.4) was introduced into the wave measurement container. Then, while a surface acoustic wave of 198 MHz was supplied to the active and standard substrates through an oscillator, frequencies of the surface acoustic waves emitted from the active and standard substrates were respectively measured according to time using an oscillator circuit. Then, 210 seconds after the setting of the base line, a PBS solution (8 g NaCl, 0.2 g KCl, 1.44 g $Na_2HPO_4$ and 0.24 g $KH_2PO_4$ in 800 ml $H_2O$, pH 7.4) was introduced into the wave measurement container. Then, while the surface acoustic wave of 198 MHz was supplied to the active and standard substrates through the oscillator, frequencies of the surface acoustic waves emitted from the active and standard substrates were respectively measured according to time using the oscillator circuit. Then, 360 seconds after the setting of the base line, a PBS solution including 1 µg HBsAb/ml (8 g NaCl, 0.2 g KCl, 1.44 g $Na_2HPO_4$ and 0.24 g $KH_2PO_4$ in 800 ml $H_2O$, pH 7.4) was introduced into the wave measurement container. Then, while the surface acoustic wave of 198 MHz was supplied to the active and standard substrates through the oscillator, frequencies of the surface acoustic waves emitted from the active and standard substrates were respectively measured according to time using the oscillator circuit.

In addition, an experiment to see how air bubbles affect the measurement of the surface acoustic wave if air bubbles were introduced into the wave measurement container was performed. Fifteen minutes after the setting of the base line, air bubbles were injected into a piezoelectric substrate in the wave measurement container by using a syringe. Then, while the surface acoustic wave of 198 MHz was supplied to the piezoelectric substrate through the oscillator, the frequency of the surface acoustic wave emitted from the piezoelectric substrate was measured according to time using the oscillator circuit.

Figure 6A:
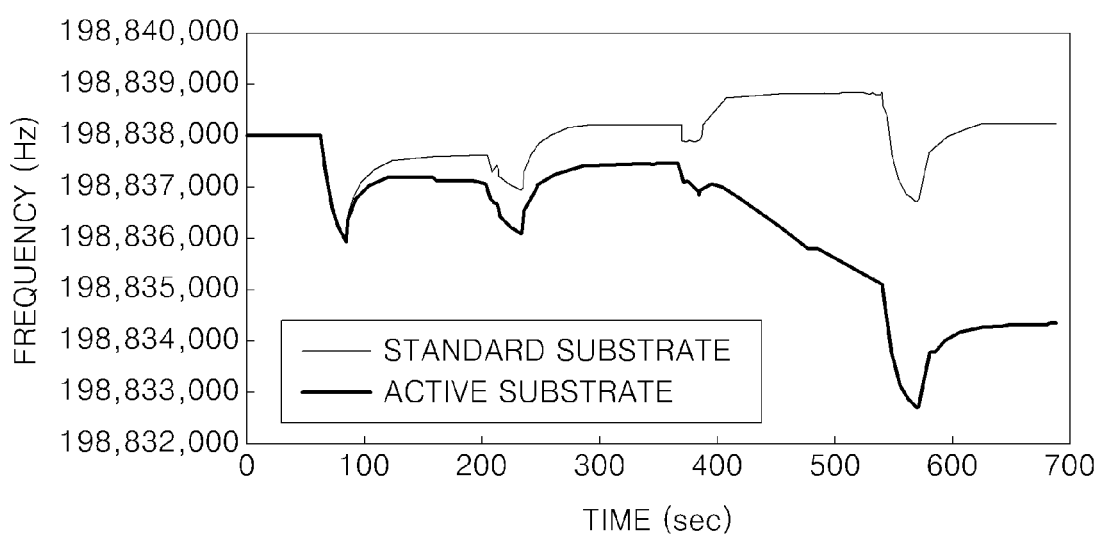
FIGS. 6A, 6B, and 6C are graphs showing how a target material in a liquid sample or air bubbles affect a surface acoustic wave.
Figure 6B:
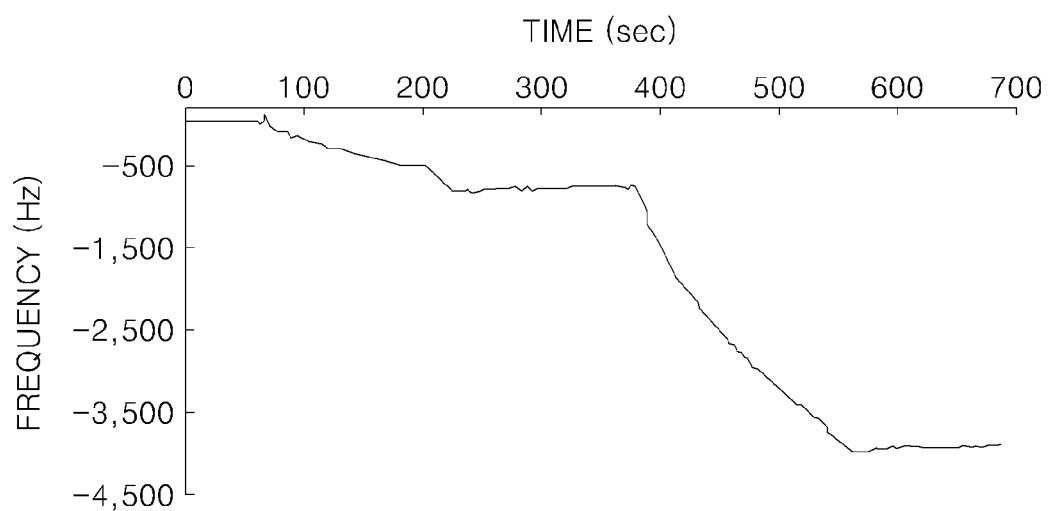
Figure 6C:
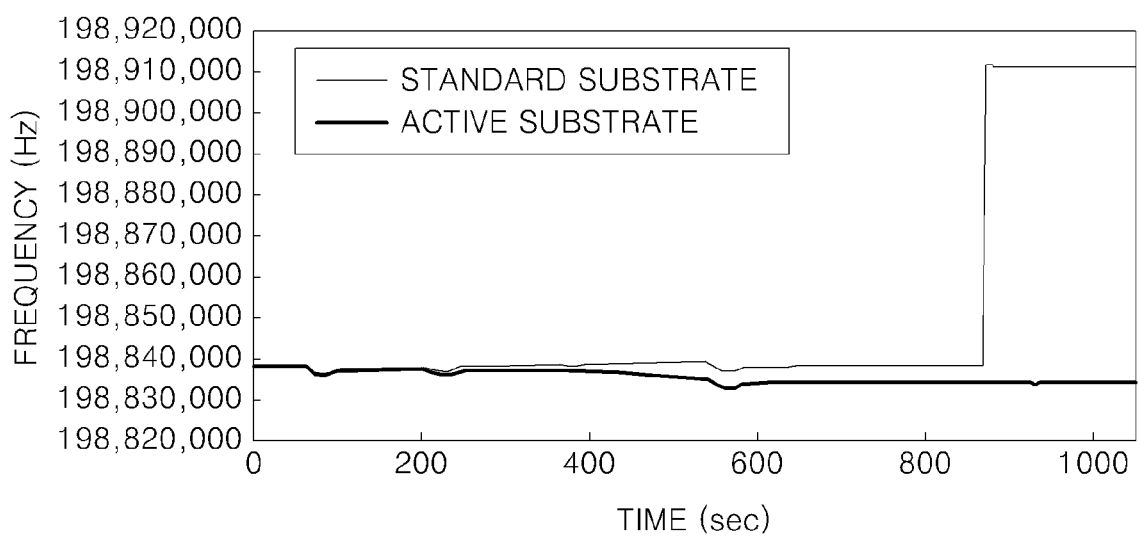

FIGS. 6A, 6B, and 6C are graphs showing how a target material in a liquid sample or air bubbles affect a surface acoustic wave.

FIG. 6A is a graph showing a change in frequency of a surface acoustic wave according to an introduction of a target liquid sample and a washing solution. Referring to FIG. 6A, when the PBS solution including 100 ng HBsAb/ml (8 g NaCl, 0.2 g KCl, 1.44 g $Na_2HPO_4$ and 0.24 g $KH_2PO_4$ in 800 ml $H_2O$, pH 7.4) was injected into the wave measurement container at the point of 60 second, the frequencies of the surface acoustic waves generated from the active and standard substrates differed. After the active and standard substrates were washed using a PBS washing solution at the point of 210 second, there was no the difference between the frequencies of the surface acoustic waves generated from the active and standard substrates. When the PBS solution including 1 µg HBsAb/ml (8 g NaCl, 0.2 g KCl, 1.44 g $Na_2HPO_4$ and 0.24 g $KH_2PO_4$ in 800 ml $H_2O$, pH 7.4) was injected into the wave measurement container at the point of 360 second, the rate of divergence between the frequencies of the surface acoustic waves generated from the active and standard substrates was greater than when the PBS solution including 100 ng HBsAb/ml (8 g NaCl, 0.2 g KCl, 1.44 g $Na_2HPO_4$ and 0.24 g $KH_2PO_4$ in 800 ml $H_2O$, pH 7.4) was used.

In particular, FIG. 6B is a graph showing the difference between the frequencies of the surface acoustic waves generated from the active and standard substrates, measured in FIG. 6A.

In particular, FIG. 6C is a graph showing frequencies of the surface acoustic waves generated from the active and standard substrates, when air bubbles were directly introduced into the wave measurement container at the point of about 900 second in the graph of FIG. 6A. As illustrated in FIG. 6C, it was confirmed that due to the introduction of the air bubbles, the difference between the frequencies of the surface acoustic waves generated from the active and standard substrates was greater than the difference in the frequencies illustrated in FIG. 6B. Therefore, air bubbles should be prevented from entering the wave measurement container.

EXAMPLE 3

Impact of Using a Wave Sensor Apparatus on Detecting Target Material in Liquid Sample Experiments on when influx and efflux of a liquid sample into and out of the wave measurement container was manually controlled and controlled using a wave sensor apparatus, in detecting a target material in the liquid sample were performed, and the results of each experiment were confirmed. A PBS solution (8 g NaCl, 0.2 g KCl, 1.44 g $Na_2HPO_4$ and 0.24 g $KH_2PO_4$ in 800 ml $H_2O$, pH 7.4) was used as a standard liquid sample and a washing solution. A PBS solution including 100 ng HBsAb/ml (8 g NaCl, 0.2 g KCl, 1.44 g $Na_2HPO_4$ and 0.24 g $KH_2PO_4$ in 800 ml $H_2O$, pH 7.4) was used as a target liquid sample. Each experiment was repeated 10 times.

A syringe was used in the experiment that was manually performed, the wave sensor apparatus used in Example 3 was the same as described in Example 1. One-time experiment set was as follows: a standard liquid sample was introduced into the wave measurement container; while a surface acoustic wave of 198 MHz was supplied to the active and standard substrates through an oscillator, frequencies of the surface acoustic waves emitted from the active and standard substrates were measured according to time using an oscillator circuit to set a base line; then, a PBS solution including 100 ng HBsAb/ml (8 g NaCl, 0.2 g KCl, 1.44 g $Na_2HPO_4$ and 0.24 g $KH_2PO_4$ in 800 ml $H_2O$, pH 7.4) was introduced into the wave measurement container; while the surface acoustic wave of 198 MHz was supplied to the active and standard substrates through the oscillator, frequencies of the surface acoustic waves emitted from the active and standard substrates were measured according to time using the oscillator circuit; then, the target liquid sample was removed from the wave measurement container; a PBS solution (8 g NaCl, 0.2 g KCl, 1.44 g $Na_2HPO_4$ and 0.24 g $KH_2PO_4$ in 800 ml $H_2O$, pH 7.4) was introduced into the wave measurement container; while the surface acoustic wave of 198 MHz was supplied to the active and standard substrates through the oscillator, frequencies of the surface acoustic waves emitted from the active and standard substrates were measured according to time using the oscillator circuit to set a base line.

Table 1 shows how the detection of the target material in the liquid sample using the manual method and the wave sensor apparatus affects a change in frequency of the surface acoustic wave, caused by the target material in the target liquid sample.

TABLE 1

| Experiment method | Detection time | frequency of occurrence of air bubbles | Average detection signal | Normal dispersion |
|---|---|---|---|---|
| Wave sensor apparatus | average 6 minutes | 0 time | 547 Hz | 74 Hz |
| Manual method | average 14 minutes 30 seconds | 6 times | 541 Hz (4 times) | 129 Hz (4 times) |

As shown in Table 1, when the wave sensor apparatus is used, the measured dispersion of the surface acoustic wave is significantly decreased compared to when the detection of the target material in the liquid sample is manually performed.

As described above, according to the one or more of the above embodiments, a target material in a liquid sample can be efficiently detected.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of detecting a target material in a liquid sample by using a wave, the method comprising:
   supplying an input wave signal to a first liquid sample that does not comprise the target material, and measuring a first output wave signal from the first liquid sample;
   supplying an input wave signal to a second liquid sample that is subject to the detecting the target material, and measuring a second output wave signal from the second liquid sample; and
   comparing the first output wave signal with the second output signal to determine whether there is a difference between the signals,
   wherein the input wave signals supplied to the first liquid sample and to the second liquid sample have the same frequency and intensity;
   wherein the output wave signal is measured after a gas in the first and second liquid samples is removed,
   wherein the first output wave signal is used as a signal base line, and
   wherein a magnitude of the difference between the signals is proportional to an amount of the target material in the second liquid sample.

2. The method of claim 1, wherein the wave signal is a surface acoustic wave signal.

3. The method of claim 2, wherein an output surface acoustic wave signal is measured from a material with a surface ("surface material"), said surface material being included in the first liquid sample and the second liquid sample.

4. The method of claim 3, wherein the surface material comprises a substance that specifically or non-specifically binds the target material, said substance ("target binding material") being immobilized on the surface of the surface material.

5. The method of claim 3, wherein the surface material comprises a surface (I) on which a target binding material is immobilized, or a surface (II) on which a non-reactive material that does not bind any components contained in the second liquid sample is immobilized.

6. The method of claim 1, wherein the first liquid sample has the same or substantially same properties to those of the second liquid sample, except that the first liquid sample does not comprise the target material.

7. The method of claim 1, wherein the measuring the output wave signals from the first liquid sample and from the second liquid sample are sequentially performed in a single wave measurement container.

8. A method of detecting a target material in a liquid sample by using a wave, the method comprising:
   supplying an input wave signal to a first liquid sample that does not comprise the target material, and measuring a first output wave signal from the first liquid sample;
   removing a gas from a second liquid sample that is subject to the detecting the target material prior to introducing the second liquid sample into the wave measurement container;
   supplying an input wave signal to the second liquid sample, and measuring a second output wave signal from the second liquid sample; and
   comparing the first output wave signal with the second output signal to determine whether there is a difference between the signals,
   wherein the input wave signals supplied to the first liquid sample and to the second liquid sample have the same frequency and intensity;
   wherein the first output wave signal is used as a signal base line, and
   wherein a magnitude of the difference between the signals is proportional to an amount of the target material in the second liquid sample.

9. The method of claim 8, which further comprises removing a gas from the first and second liquid samples by transferring at least parts of the first and second liquid samples to another container other than the wave measurement container.

10. The method of claim 5, wherein the surface material further comprises a surface (III) which does not have either of the target binding material or the non-reactive material,
    wherein the method comprises measuring an output acoustic wave signal (I) from the surface (I); and an output acoustic wave signal (II) from the surface (II), or an output acoustic wave signal (III) from the surface (III), respectively, and
    wherein the method further comprises subtracting the output acoustic wave signal (II) or (III) from the output acoustic wave signal (I).

11. The method of claim 10, wherein the surfaces (I), and (II) or (III) are included in a single wave measurement container.

12. A method of detecting a target material in a sample by a wave, the method comprising:
    applying an input wave signal to the sample and measuring an output wave signal generated from the sample; and
    comparing the output wave signal to a reference output wave signal, said reference output wave signal is an output wave signal indicative of the absence of the target material under the same measuring condition, to detect the target material in the sample,
    wherein the measuring the output wave signal comprises removing a gas in the sample.

13. The method of claim 12, wherein the applying the input wave signal and the measuring the output wave signal are performed in a single wave measurement container, and wherein the removing the gas comprises removing the gas before the sample is introduced into the wave measurement container.

14. The method of claim 13, wherein the removing the gas is performed by transferring at least a part of the sample to another container from a path through which the sample flows into the wave measurement container.

15. A wave sensor apparatus comprising a container into which a liquid sample is introduced, a wave providing unit that provides the container with a wave signal, and a wave measuring unit that measures the wave signal from the container, wherein the wave sensor apparatus further comprises a unit for removing a gas in the liquid sample introduced into the container.

16. The wave sensor apparatus of claim 15, wherein the wave signal comprises a surface acoustic wave signal.

17. The wave sensor apparatus of claim 15, wherein the container comprises a material with a surface ("surface material").

18. The wave sensor apparatus of claim 17, wherein the surface material comprises a surface on which a substance that binds the target material ("target binding material") is immobilized.

19. The wave sensor apparatus of claim 17, wherein the surface material comprises at least one of a surface (I) on which the target binding material is immobilized, a surface (II) on which a non-reactive material that does not bind any components contained in the second liquid sample is immobilized, and a surface (III) on which either of the non-reactive material or the target binding material is immobilized.

20. The wave sensor apparatus of claim 15, wherein the unit for removing the gas comprises a waste chamber used for bypassing the sample from a path through which the sample flows into the container, before the introduction of the sample to the container.

21. The wave sensor apparatus of claim 20, which further comprises a liquid sample chamber configured to receive the sample and a channel which is connected to the waste chamber and is disposed between the liquid sample chamber and the container.

22. The wave sensor apparatus of claim 15, further comprising at least one chamber selected from the group consisting of a first liquid sample chamber to receive and store a liquid sample to be tested for the detection of a target material, a second liquid sample chamber to receive and store a reference liquid sample, and a washing chamber comprising a washing solution.

* * * * *